US007659423B1

(12) United States Patent
McArdle

(10) Patent No.: US 7,659,423 B1
(45) Date of Patent: Feb. 9, 2010

(54) METHOD OF PREPARING ELECTRON DEFICIENT OLEFINS IN POLAR SOLVENTS

(75) Inventor: Ciaran B. McArdle, Dublin (IE)

(73) Assignee: Loctite (R&D) Limited, Dublin (IE)

( * ) Notice: Subject to any disclaimer, the term of this patent is extended or adjusted under 35 U.S.C. 154(b) by 640 days.

(21) Appl. No.: 11/379,103

(22) Filed: Apr. 18, 2006

(51) Int. Cl.
*C07C 255/00* (2006.01)
(52) U.S. Cl. .................... 558/443; 558/375; 558/381
(58) Field of Classification Search ............... 558/443, 558/375, 381
See application file for complete search history.

(56) References Cited

U.S. PATENT DOCUMENTS

| 2,363,464 A | 11/1944 | Senkus |
| 2,413,249 A | 12/1946 | Senkus |
| 2,413,250 A | 12/1946 | Senkus |
| 2,415,046 A | 1/1947 | Senkus |
| 2,582,128 A | 1/1952 | Hurwitz |
| 2,721,858 A | 10/1955 | Joyner et al. |
| 2,756,251 A | 7/1956 | Joyner et al. |
| 2,763,677 A | 9/1956 | Jeremias |
| 3,142,698 A | 7/1964 | Halpern et al. |
| 3,903,055 A | 9/1975 | Buck |
| 3,975,422 A | 8/1976 | Buck |
| 3,988,299 A | 10/1976 | Malofsky |
| 4,003,942 A | 1/1977 | Buck |
| 4,012,402 A | 3/1977 | Buck |
| 4,013,703 A | 3/1977 | Buck |
| 4,202,920 A | 5/1980 | Renner et al. |
| 4,364,876 A | 12/1982 | Kimura et al. |
| 4,512,357 A | 4/1985 | Earl |
| 4,556,700 A | 12/1985 | Harris et al. |
| 4,587,059 A | 5/1986 | Harth et al. |
| 4,622,414 A | 11/1986 | McKervey |
| 4,636,539 A | 1/1987 | Harris et al. |
| 4,695,615 A | 9/1987 | Leonard et al. |
| 4,718,966 A | 1/1988 | Harris et al. |
| 4,837,260 A | 6/1989 | Sato et al. |
| 4,855,461 A | 8/1989 | Harris |
| 4,906,317 A | 3/1990 | Liu |
| 5,142,098 A | 8/1992 | Bru-Magniez et al. |
| 5,288,794 A | 2/1994 | Attarwala |
| 5,306,752 A | 4/1994 | Attarwala |
| 5,312,864 A | 5/1994 | Wenz et al. |
| 5,328,944 A | 7/1994 | Attarwala et al. |
| 5,424,343 A | 6/1995 | Attarwala |
| 5,424,344 A | 6/1995 | Lewin |
| 5,455,369 A | 10/1995 | Meier et al. |
| 5,624,699 A | 4/1997 | Lang |
| 5,703,267 A | 12/1997 | Takahashi et al. |
| 5,744,642 A | 4/1998 | Lantzsch et al. |
| 6,093,780 A | 7/2000 | Attarwala |
| 6,096,848 A * | 8/2000 | Gololobov et al. .......... 526/298 |
| 6,245,933 B1 * | 6/2001 | Malofsky et al. ............ 558/381 |
| 6,291,544 B1 * | 9/2001 | Kotzev ...................... 522/173 |
| 6,835,789 B1 | 12/2004 | Kneafsey et al. |

| 2006/0094833 A1 | 5/2006 | McDonnell et al. |

FOREIGN PATENT DOCUMENTS

| EP | 0 459 617 A1 | 12/1991 |
| WO | WO 94/15590 A1 | 7/1994 |
| WO | WO 95/32183 | 11/1995 |
| WO | WO 99/14206 A1 | 3/1999 |
| WO | WO 03/006225 A1 | 1/2003 |
| WO | WO 03/086605 A2 | 10/2003 |

OTHER PUBLICATIONS

Carl J. Buck, Unequivocal Synthesis of Bis(2-Cyanoacrylate) Monomers. I. Via Anthracene Adducts, *Journal of Polymer Science, Polymer Chemistry Edition*, vol. 16, pp. 2475-2507 (1978).
G. Jones, "The Knoevenagle Condensation", *Organic Reactions*, vol. XV, 204, Wiley New York (1967).
F. Bigi et al., "Montmorillonite KSF as an Inorganic, Water Stable, and Reusable Catalyst for the Knoevenagel Synthesis of Coumarin-3-carboxylic Acids", *Journal Organic Chemistry*, vol. 64 p. 1033-1035 (1999).
B. Green et al., "Synthesis of Steroidal 16,17-Fused Unsaturated δ-Lactones[1]", *Journal Organic Chemistry*, vol. 50, p. 640-644 (1985).
P. Rao et al., "Zinc Chloride As A New Catalyst For Knoevenagel Condensation", *Tetrahedron Letters*, vol. 32, No. 41, p. 5821-5822 (1991).
L. Tietze et al., Comprehensive Organic Synthesis, Pergamon Press, Oxford, vol. 2, Chapter 1.11, p. 341 (1991).
P. Laszlo, "Catalysis of Organic Reactions by Inorganic Solids", *Accounts of Chemical Research*, vol. 19, p. 121-127 (1986).
K. Kloestra et al., "Base and Acid Catalysis by the Alkali-containing MCM-41 Mesoporous Molecular Sieve", *Journal Chemical Soc. Chem. Commun.*, p. 1005-1006 (1995).
P. Lednor et al., "The Use of a High Surface Area Silicon Oxynitride as a Solid, Basic Catalyst", *Journal Chemical Society, Chem. Commun.*, pp. 1625-1626 (1991).
F. Bigi et al., "A Revision of the Biginelli Reaction Under Solid Acid Catalysis. Solvent-free Synthesis of Dihydropyrimidines Over Montmorillonite KSF", *Tetrahedron Letters*, vol. 40, pp. 3465-3468 (1999).
F. Bigi et al., "Clean synthesis in water: uncatalysed preparation of ylidenemalononitriles", *Green Chemistry*, vol. 2, p. 101-103 (2000).
R. Breslow, "Hydrophobic Effects on Simple Organic Reactions in Water" *Accounts of Chemical Research*, vol. 24, p. 159-164 (1991).
C. Li, "Organic Reactions in Aqueous Media—With a Focus on Carbon-Carbon Bond Formation", *Chemical Reviews*, vol. 93, p. 2023-2035 (1993).
T. Welton, "Room Temperature Ionic Liquids. Solvents for Synthesis and Catalysis", *Chemical Reviews*, vol. 99, p. 2071-2083 (1999).
D. Morrison et al., "Base-promoted reactions in ionic liquid solvents. The Knoevenagel and Robinson annulation reactions", *Tetrahedron Letters*, vol. 42, pp. 6053-6055 (2001).
Fraga-Dubreiul et al., "Grafted ionic liquid-phase-supported synthesis of small organic molecules", *Tetrahedron Letters*, vol. 42, pp. 6097-6100 (2001).

(Continued)

*Primary Examiner*—Peter G O'Sullivan
*Assistant Examiner*—Sudhakar Katakam
(74) *Attorney, Agent, or Firm*—Steven C. Bauman

(57) ABSTRACT

This invention relates to a process for producing electron deficient olefins, such as 2-cyanoacrylates, in a polar solvent, such as an ionic liquid.

16 Claims, No Drawings

OTHER PUBLICATIONS

M. Smietana et al., "Preparation of Silyl Enol Ethers Using (Bistrimethylsilyl)acetamide in Ionic Liquids", *Organic Letters*, vol. 3, No. 7, p. 1037-1039 (2001).

Li et al., "*n*-Butyl Pyridinium Nitrate as a Reusable Ionic Liquid Medium for Knoevenagel Condensation", *Chinese Chemical Letters*, vol. 14, No. 5, p. 448-450 (2003).

J. Harjani et al., "Lewis acidic ionic liquids for the synthesis of electrophilic alkenes via the Knoevenagel condensation" *Tetrahedron Letters*, vol. 43, pp. 1127-1130 (2002).

Xu et al., "Knoevenagel condensation Reaction Catalyzed by Functionalized Ionic Liquid 1-(2-Hydroxyethyl)-3-methyl Imidazolium Chloride", *Chinese Journal of Organic Chemistry*, vol. 24(10), p. 1253-1256(2004).

Su et al., "Organic Reactions in Ionic Liquids: Knoevenagel Condensation Catalyzed by Ethylenediammonium Diacetate", *Synthesis 2003*, No. 4, pp. 555-559 (2003).

Yadav et al., Phosphane-Catalized Knoevenagel Condensation: A Facile Synthesis of α-Cyanoacrylates and α-Cyanonitriles, *European Journal Organic Chemistry*, pp. 546-551 (2004).

Carl J. Buck, Unequivocal Synthesis of Bis(2-Cyanoacrylate) Monomers, I. Via Anthracene Adducts, *Journal of Polymer Science, Polymer Chemistry Edition*, vol. 16, 2475-507 (1978).

B. Green et al., Synthesis of Steroidal 16, 17-Fused Unsaturated δ-Lactones[1],*Journal Organic Chemistry*, vol. 50, 640-44 (1985).

P. Rao et al., "Zinc Chloride As A New Catalyst For Knoevenagel Condensation", *Tetrahedron Letters*, vol. 32, No. 41, 5821-22 (1991).

J. S. Yadav et al., "Phosphane-Catalyzed Knoevenagel Condensation: A Facile Synthesis of Cyanoacrylates and α-Cyanonitriles", *European Journal Organic Chemistry*, 546-51 (2004).

L. Tietze et al., Comprehensive Organic Synthesis, Pergamon Press, Oxford, vol. 2, Chapter 1.11, 341 (1991).

P. Laszlo, "Catalysis of Organic Reactions by Inorganic Solids", *Accounts of Chemical Research*, vol. 19, 121-27 (1986).

K. Kloestra et al., "Base and Acid Catalysis by the Alkali-containing MCM-41 Mesoporous Molecu Sieve", *Journal Chemical Soc. Chem. Commun.*, 1005-06 (1995).

P. Lednor et al., "The Use of a High Surface Area Silicon Oxynitride as a Solid, Basic Catalyst", *Journal Chemical Society, Chem. Commun.*, 1625-26 (1991).

F. Bigi et al., "A Revision of the Biginelli Reaction Under Solid Acid Catalysis. Solvent-free Synthesis Of Dihydropyrimidines Over Montmorilionite KSF", *Tetrahedron Letters*, vol. 40, 3465-68 (1999).

F. Bigi et al., "Clean synthesis in water: uncatalysed preparation of ylidenemalononitriles", *Green Chemistry*, vol. 2, 101-03 (2000).

R. Breslow, "Hydrophobic Effects on Simple Organic Reactions in Water", *Accounts of Chemical Research*, vol. 24, 159-64 (1991).

C. Li, "Organic Reactions in Aqueous Media—With a Focus on Carbon-Carbon Bond Formation", *Chemical Reviews*, vol. 93, 2023-35 (1993).

T. Welton, "Room Temperature Ionic Liquids. Solvents for Synthesis and Catalysis", *Chemical Reviews*, vol. 99, 2071-83 (1999).

D. Morrison et al., "Base-promoted reactions in ionic liquid solvents. The Knoevenagel and Robinson annulation reactions", *Tetrahedron Letters*, vol. 42, 6053-55 (2001).

Fraga-Dubreiul et al., "Grafted ionic liquid-phase-supported synthesis of small organic molecules", *Tetrahedron Letter*, vol. 42, 6097-6100 (2001).

M. Smietana et al., "Preparation of Silyl Enol Ethers Using (Bistrimethylsilyl)acetamide in Ionic Liquids", *Organic Letters*, vol. 3, No. 7, 1037-39 (2001).

Li et al., "*n*-Butyl Pyridinium Nitrate as a Reusable Ionic Liquid Medium for Knoevenagel Condensation", *Chinese Chemical Letters*, vol. 14, No. 5, 448-50 (2003).

J. Harjani et al., "Lewis acidic ionic liquids for the synthesis of electrophilic alkenes via the Knoevenagel condensation", *Tetrahedron Letters*, vol. 43, 1127-30 (2002).

Xu et al., "Knoevenagel condensation Reaction Catalyzed by Functionalized Ionic Liquid 1-(2-Hydroxyethyl)-3-methyl Imidazolium Chloride", *Chinese Journal of Organic Chemistry*, vol. 24(10), 1253-56 (2004).

Su et al., "Organic Reactions in Ionic Liquids: Knoevenagel Condensation Catalyzed by Ethylenediammonium Diacetate", *Synthesis 2003*, No. 4, 555-59 (2003).

Moehrle et al., "Aminomethylierung von 1,3-Diketonen", *Pharmazie*, vol. 40, 697-701 (1985).

J. March, "Reactions", *Advanced Organic Chemistry*, 3rd Edition, Wiley & Sons Inc., 417 (1985).

J. March, "Addition to Carbon-Hetero Multiple Bonds", *Advanced Organic Chemistry*, 3rd Edition, Wiley & Sons, 802-03 (1985).

M. B. Smith, *Organic Synthesis*, McGraw Hill International Chemistry Series, 1302 (1994).

Tehrani et al., "Product Class 8: Iminium Salts", *Science of Synthesis*, vol. 27, 313-48 (2004).

B. Hin et al., "Facile Synthesis of α-Substituted Acrylate Esters", *Journal of Organic Chemistry*, vol. 67, 7365-68 (2002).

Holy et al., "The Mannich Reaction-II Derivatization of Aldehydes and Ketones Using Dimethyl(methylene)ammonium Salts", *Tetrahedron Letters*, vol. 35, 613-19 (1979).

Bryson et al., "Preformed Mannich Salts: A Facile Preparation of Dimethyl(methylene)ammonium Iodide", *Journal of Organic Chemistry*, vol. 45, 524-25 (1980).

J. March, "The Pinacol Rearrangement", *Advanced Organic Chemistry*, 3rd Edition, Wiley & Sons, 963-64 (1985).

J. March, "Free-Radical Substitution", *Advanced Organic Chemistry*, 3rd Edition, Wiley & Sons, 642 (1985).

Jahn et al., "A Novel and Simple Method for the Preparation of Iminium Salts", *Tetrahedron Letters*, vol. 34, No. 37, 5863-66 (1993).

R. J. Vijin et al., Synthesis, 573 (1994).

Davis, "Chemistry Letters", vol. 33, Issue 9, 1072-77 (2004).

Davis et al., "Ionic Liquids in Synthesis", P. Wasserscheid and T. Welton, eds., Wiley-VCH Verlag GmbH & Co. KGaA, Chapter 2 (2002).

M.G. Djamali, P. Burba, K.H. Lieser, "Snythese und Eigenschaften eines Celluloseaustauschers mit Diaminodibenzo-18-Krone-6 als Ankergruppe", Die Angewandte Makromolecular Chemie, vol. 92, 145-54 (1980).

K. Babic, "Reactive and Functional Polymers", vol. 66, 1494-1505 (2006).

Trumbo et al., "Copolymerization Behavior of 3-Isopropenyl-α,α-Dimethylbenzylamine and Preliminary Evaluation of the Copolymers in Thermoset Coatings", *Journal of Applied Polymer Science*, vol. 82, 1030-39 (2001).

T. Giesenberg et al., "Synthesis and Functionalization of a New Kind of Silica Particle." *Agnew. Chem. Int. Ed.*, 43, 5697-5700 (2004).

Zhang et al., "An Investigation of Knoevenagel condensation reaction in microreactors using a new zeolite catalyst", *Applied Catalysis A: General*, 261, 109-118 (2004).

Mehnert et al., "Chemical Communications", 3010 (2002).

Lee and Lee, "Bulletin of the Korean Chemical Society", vol. 25, Issue 10, 1531-37 (2004).

H. R. Snyder and W. E. Hamlin, "Alkylation of Nitroparaffins with Amines and Their Derivatives", *Journal of American Chemical Society*, vol. 72, 5082-85 (1950).

H. G. Johnson, "Reaction of Aliphatic Amines with Formaldehyde and Nitroparaffins. II. Secondary Amines", *Journal of American Chemical Society*, vol. 68, 12-14 (1946).

M. Semkus, "Journal of the American Chemical Society", vol. 68, 10-12 (1946).

Sarac, "Progress in Polymer Science", vol. 24, 1149-1201(1999).

Brough et al., "Pyrimidinyl Nitronyl Nitroxides", *Chemical European Journal*, vol. 12, 5134 (2006).

Zhou et al., *J. Polym. Sci., Part A Polym. Chem. Ed.*, 29, 1097 (1991).

Mehrotra et al., "Journal of Organometalic Chemistry", vol. 24, 611-21 (1970).

Son et al., "Synthesis of Hexahydro-3,3,5,5,7-pentaalkyI-2H-1,4-diazepin-2-ones from 1,3-Diamines And Ketones", *J. Org. Chem.*, vol. 46, 323 (1981).

Senkus, Acetals of Nitro Alcohols and Corresponding Amino Acetals, *J. Amer. Chem. Soc.*, vol. 69, 1380-81 (1947).

Renner et al., "Cure of Epoxy Resins with Esters of Cyanoacrylic Acid", *Journal of Polymer Science: Polymer Chemistry Edition*, vol. 23, 2341 (1985).

Kennedy et al., "Macromers by Carbocationic Polymerization. X. Synthesis, Characterization, and Polymerizability of Cyanoacrylate-Capped Polyisobutylenes", *Journal of Macromolecular Science, Part A*, 28:2, 209-24 (1991).

Khrustalev et al., "Synthesis and X-ray structural study of 1-adamantylmethy 2-cyanoacrylatel And 1,10-decanediol bis-2-cyanoacrylate", *Russian Chemical Bulletin*, vol. 45, No. 9, 2172 (1996).

Y. Gololobov et al., "A novel approach to the synthesis of bis(2-cyanoacrylates)", *Russian Chemical Bulletin*, vol. 42, No. 5, 961 (1993).

Y. Gololobov et al., "Synthesis of bis(2-cyanoacrylates) from 2-cyanoacryloyl chloride and 2-butene-and 2-butyne-1,4-diols", *Russian Chemical Bulletin*, vol. 44, No. 4, 760 (1995).

J.-L. De Keyser et al., "A Versatile and Convenient Multigram Synthesis of Methylidenemalonic Acid Diesters", *J. Org. Chem.*, vol. 53, 4859 (1988).

Vijayalakshmi et al., "Alkyl and substituted alkyl 2-cyanoacrylates. Part I. Synthesis and Properties", *J. Adhesion Science Technology*, vol. 4, No. 9, 733 (1990).

Guseva et al., "Organic Chemistry. Synthesis of functionality substituted cyanoacetates." *Russian Chemical Bulletin*, vol. 42, No. 3, 478 (1993).

Guseva et al., "Organic Chemistry" *Russian Chemical Bulletin*, vol. 43, No. 4, 595 (1995).

Gololobov and Gruber, Russian Chemical Review, vol. 66, Issue 11, 953 (1997).

Senchenya et al., "Silicon-containing esters of $\alpha$-cyanoacrylic acid: synthesis and properties" *Russian Chemical Bulletin*, vol. 42, No. 5, 909 (1993).

Bowie J. H. et al., "Tetrahedron", vol. 23, 305-20 (1967).

J. S. Norwick et al., J. Org. Chem., 57(28), 7364-66 (1992).

* cited by examiner

METHOD OF PREPARING ELECTRON DEFICIENT OLEFINS IN POLAR SOLVENTS

BACKGROUND OF THE INVENTION

1. Field of the Invention

This invention relates to a process for producing electron deficient olefins, such as 2-cyanoacrylates, in a polar solvent, such as an ionic liquid.

2. Brief Description of Related Technology

Cyanoacrylate adhesives are known for their fast adhesion and ability to bond a wide variety of substrates. They are marketed as "super glue" type adhesives. They are useful as an all-purpose adhesive since they are a single component adhesive, very economical as only a small amount will do, and generally do not require any equipment to effectuate curing.

Traditionally, cyanoacrylate monomers are produced by way of a Knoevenagel condensation reaction between a formaldehyde precursor, such as paraformaldehyde, and an alkyl cyanoacetate with a basic catalyst. During the reaction, monomer forms and polymerises in situ to a prepolymer that is subsequently thermally cracked or depolymerised into the pure constituent monomer. This approach has remained essentially the same although various improvements and variants have been more recently introduced. See e.g. U.S. Pat. Nos. 6,245,933, 5,624,699, 4,364,876, 2,721,858, 2,763,677 and 2,756,251.

In U.S. Pat. No. 3,142,698, the synthesis of difunctional cyanoacrylates using a Knoevenagel condensation is described. However the ability to thermally depolyerise the resulting, now crosslinked, prepolymer in a reliable and reproducible manner to produce pure difunctional monomers in high yields is questionable [see J. Buck, *J. Polym. Sci.*, Polym. Chem. Ed., 16, 2475-2507 (1978), and U.S. Pat. Nos. 3,975,422, 3,903,055, 4,003,942, 4,012,402, and 4,013,703].

A variety of other processes for producing cyanoacrylate are known, and some of which are described below.

U.S. Pat. No. 5,703,267 defines a process for producing a 2-cyanoacrylic acid which comprises subjecting a 2-cyanoacrylate and an organic acid to a transesterification reaction.

U.S. Pat. No. 5,455,369 defines an improvement in a process for preparing methyl cyanoacrylate, in which methyl cyanoacetate is reacted with formaldehyde to form a polymer that is then depolymerized to the monomeric product, and in which the purity of yield is 96% or better. The improvement of the '369 patent is reported to be conducting the process in a poly(ethylene glycol) diacetate, dipropionate, or dibutyrate, having a number average molecular weight of 200-400, as the solvent.

U.S. Pat. No. 6,096,848 defines a process for the production of a biscyanoacrylate, which comprises the steps of esterifying a 2-cyanoacrylic acid or transesterifying an alkyl ester thereof to obtain a reaction mixture; and fractionally crystallizing the reaction mixture to obtain the biscyanoacrylate.

U.S. Pat. No. 4,587,059 defines a process for the preparation of monomeric 2-cyanoacrylates comprising the steps of (a) reacting (i) a 2,4-dicyanoglutarate with (ii) formaldehyde, cyclic or linear polymers of formaldehyde, or a mixture thereof, in the presence of between about 0.5 and about 5 mols of water per mol of 2,4-dicyanoglutarate, at an acid pH of about 3 to slightly less than 7, and at a temperature of about 70 to about 140, to form an oligomeric intermediate product, and (b) removing water that is present from step (a) and thermolyzing the oligomeric intermediate product for a period of time sufficient to effect its conversion to monomeric 2-cyanoacrylates.

Commercial production of cyanoacrylate monomers ordinarily relies on the depolymerisation of a prepolymer formed under Knoevenagel reaction conditions. Previous efforts to produce cyanoacrylates explored alternative routes that do not rely on depolymerisation, for instance in the synthesis of difunctional monomers that cannot be reliably accessed by depolymerisation, or for the synthesis of esters not easily accessed by depolymerisation.

Still today the Knoevenagel condensation reaction is believed to remain the most efficient and prevalent commercial method for producing high yields of monofunctional cyanoacrylates. Nevertheless, it would be desirable to not have to resort to thermally induced depolymerisation of a prepolymer produced by the Knoevenagel condensation reaction. This prospect would also enable facile access to highly useful difunctional monomers, such as so-called bis-cyanoacrylates or hybrid materials of cyanoacrylate and other polymerisable or reactive functions.

The Knoevenagel reaction is well known not only for its usefulness in the manufacture of cyanoacrylates, but also (and perhaps more so) for its immense potential generally in the synthesis of electrophilic olefins from active methylene and carbonyl compounds [G. Jones, *Organic Reactions*, Vol. XV, 204, Wiley, New York (1967)]. A wide range of catalysts have been employed in carrying out this reaction, each affording variable yields of olefins. The reaction is catalysed by weak bases under homogeneous conditions. More recently, heterogeneous catalysts have been use, many of which include inorganic materials such as clays and zeolites [F. Bigi et al., *J. Org. Chem.*, 64, 1033 (1999)]. These materials are environmentally benign and have been used because they are ditopic in nature, some containing both acidic and basic sites, while others are soley acidic or soley basic. Some Lewis acid catalysts have also been employed in the Knoevenagel reaction [B. Green et al., *J. Org. Chem.*, 50, 640 (1985); P. Rao et al., *Tett. Lett.*, 32, 5821 (1991)]. Since bases are generally active nucleophiles and cyanoacrylate monomer is highly susceptible to initiation of polymerisation by active nucleophiles, it is not possible to exploit base catalysed Knoevenagel synthesis of cyanoacrylate monomer without polymerisation occurring. And while acid catalysed Knoevenagel condensation reactions to form cyanopentadienoate monomers (related to cyanoacrylates) are known (see e.g. U.S. Pat. No. 6,291,544), these routes do not lead to the direct synthesis of cyanoacrylate monomers per se.

The Knoevenagel reaction also liberates water during the condensation of aldehydes with reactive methylene compounds, and neutral and basic water is well known to initiate polymerisation of cyanoacrylate monomers.

The efficiency of the Knoevenagel reaction is also known to be highly solvent dependent and that usually dipolar aprotic solvents, like dimethylformamide or dimethylsulfoxide, or especially useful in this condensation, because the second step, a 1,2-elimination has been reported to be inhibited by protic solvents [L. Tietze and U. Beifuss, *Comprehensive Organic Synthesis*, B. Trost et al., eds., Pergamon Press, Oxford, Vol. 2, Chapter 1.11, 341 (1991)]. The aforementioned solvents are toxic, teratogenic and suspected carcinogens, and can initiate cyanoacrylate polymerisation, thus their usage is disfavoured on a commercial scale.

Notwithstanding the reported inhibition by protic solvents, various authors have found that the Knoevenagel reaction easily occurs in protic media and also in water, even though this reaction remarkably involves a net dehydration [see e.g.

F. Bigi et al., *J. Org. Chem.*, 64, 1033 (1999), P. Laszlo, *Ac Chem. Res.*, 19, 121 (1986), K. Kloestra et al., *J. Chem. Soc., Chem. Commun.*, 1005 (1995), P. Lednor et al., *J. Chem. Soc., Chem. Commun.*, 1625 (1991), and F. Bigi et al., *Tett. Lett.*, 40, 3465 (1999)].

Recently there have been reports of the use of polar aprotic and protic solvents, including water, in uncatalysed Knoevenagel reactions leading to excellent yields and selectivities in the formation of products dervied from malononitrile and mainly aromatic aldehydes, although some aliphatic aledhehydes were reported on [F. Bigi et al., *Green Chem.*, 2, 101 (2000)]. The use of water as a solvent in organic chemistry has received increasing attention in the past decade [see e.g. R. Breslow, *Ac Chem. Res.*, 24, 159 (1991) and Li, *Chem. Rev.*, 93, 2023 (1993)], however a large excess of neutral and basic aqueous reaction media would initiate polymerisation in the Knoevenagel synthesis of cyanoacrylate monomers even though this may offer other benefits since water is an environmentally benign, non flammable, and relatively inexpensive solvent. Thus a depolymerisation step is still required to yield pure monomer.

A highly desirable goal would be to find a solvent with some of the characteristics of water that would encourage high yields and selectivities and preferably act as a solvent-catalyst for the Knoevenagel reaction of electron deficient olefins, such as cyanoacrylates, without resort to a depolymerisation step. If necessary, acidic (e.g. Lewis) catalysts may be used in conjunction with such a solvent, as could common dehydrating agents that would react with water liberated from the Knoevenagel reaction proper.

Several publications have shown that replacing organic solvents by ionic liquids can lead to improvements in well known procedures [T. Welton, *Chem Rev.*, 99, 2071 (1999), D. Morrison et al., *Tet. Lett.*, 42, 6053 and 6097 (2001), and M. Smietana et al., *Org. Lett.*, 3, 1037 (2001)]. Indeed, ionic liquids have been used with some success as solvents in Knoevenagel reactions. For example, n-butyl pyridinium nitrate has been used as a solvent to replace conventional organic solvents in the Knoevenagel condensation of various carbonyl substrates with active methylene compounds [Y-Q Li et al., *Chinese Chem. Letts.*, 14, 5, 448 (2003)]. The ionic liquid, 1-butyl-3-methylimidiazolium chloroaluminate, has been used in the synthesis of electrophilic alkenes via the Knoevenagel condensation [J. Harjani et al., *Tet. Lett.*, 43, 1127 (2002)]. Functionalised ionic liquid solvents have also been used in Knoevenagel reactions [X-M Xu et al., *J. Org. Chem.*, 24(10), 1253 (2004)]. The use of ionic liquids as solvents for Knoevenagel condensation in the presence of specific catalysts for this reaction is also known [Su et al., *Synthesis*, 4, 555 (2003)].

Recently, J. S. Yadav et al., Phosphane-Catalyzed Knoevenagel Condensation: A Facile Synthesis of α-Cyanoacrylates and α-Cyanonitriles", *Eur. J. Org. Chem.*, 546-551 (2004) reports of the use of triphenylphosphane [sic, triphenylphosphine] as a catalyst for the Knoevenagel condensation of aldehydes with acidic methylene compounds, such as ethyl cyanoacetate and malonitrile, to afford substituted olefins in an efficient manner under mild and solvent-free conditions. Triphenyphosphine is a known initiator for the polymerization of 2-cyanoacrylates.

However, to date, it is not believed that any one has investigated the synthesis of cyanoacrylates or other electron deficient olefins using an ionic liquid as a solvent in the Knoevenagel condensation reaction.

SUMMARY OF THE INVENTION

The present invention provides a direct or "crackless" synthesis of electron deficient olefins, such as cyanoacrylate monomers, using polar or aprotic media, such as ionic liquids. The synthesis hereby provided may be catalysed or uncatalysed, and conventionally is called a Knoevenagel condensation reaction.

The present invention provides a process for the preparation of a reactive electron deficient olefin. In one aspect, the invention includes the steps of:

(a) providing as reactants an aldehyde compound having the structure R—CH=O, where R is hydrogen or vinyl and a compound containing a methylene linkage having at least one electron withdrawing substituent attached thereto, where the electron withdrawing substituent is selected from nitrile, carboxylic acids, carboxylic esters, sulphonic acids, ketones and nitro, in a solvent comprising an ionic liquid;

(b) reacting the mixture of reactants under appropriate conditions and for a time sufficient to yield a reactive electron deficient olefin; and (c) separating from the mixture the so formed reactive electron deficient olefin to yield the reactive electron deficient olefin substantially free from reactants.

In another aspect, the invention includes the steps of:

(a) providing as reactants an aldehyde compound having the structure R—CH=O, where R is hydrogen or vinyl and a compound containing a methylene linkage having at least one electron withdrawing substituent attached thereto, where the electron withdrawing substituent is selected from nitrile, carboxylic acids, carboxylic esters, sulphonic acids, ketones and nitro, in a solvent comprising a salt whose melting point is less than 100° C., which in its molten form contains only ions;

(b) reacting the mixture of reactants under appropriate conditions and for a time sufficient to yield a reactive electron deficient olefin; and (c) separating from the mixture the so formed reactive electron deficient olefin to yield the reactive electron deficient olefin substantially free from reactants.

In yet another aspect, the invention provides a process for the preparation of a 2-cyanoacrylate ester. The steps of this process include (a) providing as reactants an aldehyde compound (or a source of an aldehyde compound) having the structure R—CH=O, where R is hydrogen and a compound containing a methylene linkage having at least one nitrile and at least one carboxylic ester attached thereto, in a polar solvent;

(b) reacting the mixture of reactants under appropriate conditions and for a time sufficient to yield a 2-cyanoacrylate ester; and (c) separating from the mixture the so-formed 2-cyanoacrylate ester to yield 2-cyanoacrylate ester substantially free from reactants.

In any of these aspects, the process may be conducted with or without added catalyst. When a catalyst is added, desirably the catalyst should be one that is not a soley basic nucleophilic. Thus, acidic system would be preferred and a ditropic system may be used, as well.

DETAILED DESCRIPTION OF THE INVENTION

As noted above, the present invention provides a process for the preparation of a reactive electron deficient olefin. In one aspect, the invention includes the steps of:

(a) providing as reactants an aldehyde compound having the structure R—CH=O, where R is hydrogen or vinyl and a compound containing a methylene linkage having at least one electron withdrawing substituent attached thereto, where the electron withdrawing substituent is selected from nitrile, carboxylic acids, carboxylic esters, sulphonic acids, ketones and nitro, in a solvent comprising an ionic liquid;

(b) reacting the mixture of reactants under appropriate conditions and for a time sufficient to yield a reactive electron deficient olefin; and (c) separating from the mixture the so formed reactive electron deficient olefin to yield the reactive electron deficient olefin substantially free from reactants.

In another aspect, the invention includes the steps of:

(a) providing as reactants an aldehyde compound having the structure R—CH=O, where R is hydrogen or vinyl and a compound containing a methylene linkage having at least one electron withdrawing substituent attached thereto, where the electron withdrawing substituent is selected from nitrile, carboxylic acids, carboxylic esters, sulphonic acids, ketones and nitro, in a solvent comprising a salt whose melting point is less than 100° C., which in its molten form contains only ions;

(b) reacting the mixture of reactants under appropriate conditions and for a time sufficient to yield a reactive electron deficient olefin; and (c) separating from the mixture the so formed reactive electron deficient olefin to yield the reactive electron deficient olefin substantially free from reactants.

In yet another aspect, the invention provides a process for the preparation of a 2-cyanoacrylate ester. The steps of this process include (a) providing as reactants an aldehyde compound (or a source of an aldehyde compound) having the structure R—CH=O, where R is hydrogen and a compound containing a methylene linkage having at least one nitrile and at least one carboxylic ester attached thereto, in a polar solvent;

(b) reacting the mixture of reactants under appropriate conditions and for a time sufficient to yield a 2-cyanoacrylate ester; and (c) separating from the mixture the so-formed 2-cyanoacrylate ester to yield 2-cyanoacrylate ester substantially free from reactants.

In any of these aspects, the process may be conducted with or without added catalyst, as noted above.

Thus, as an initial reactant in the inventive processes are aldehyde compounds having the structure R—CH=O, where R is hydrogen or vinyl. The aldehyde compound may be an aldehyde itself or a source of an aldehyde, such as one that yields an aldehyde like formaldehyde under reaction conditions. The aldehyde compound in a desirable embodiment includes formaldehyde (or a source thereof, such as paraformaldehyde), 1,3,5-trioxane, or vinyl aldehydes such as acrolein.

As a second reactant in the inventive processes are compounds containing a methylene linkage having at least one electron withdrawing substituent attached thereto. In these compounds, the electron withdrawing substituent is selected from nitrile, carboxylic acids, carboxylic esters, sulphonic acids, ketones and nitro. In a desirable embodiment, these compounds have two or more electron withdrawing substituents, which may be the same or different, such as nitrile and carboxylic acid ester.

Representative examples include malononitrile, malonic acid and its esters, ethyl nitroacetate, cyano acetic acid and its esters, 4-cyclopentene-1,3-dione, cyclopentane-1,3-dione, 4-cyclohexene-1,3-dione, cyclohexane-1,3-dione, 2,2-dimethyl-1,3-dioxane-4,6-dione (Meldrum's acid), and tetronic acid, some of which are commercially available for instance from Aldrich Chemical Co. A particularly desirable example is 2-cyanoacetate.

The structures below illustrate the products that would result from a Knoevenagel reaction involving paraformaldehyde and/or acrolein using the above reactants.

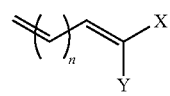

I

Here, when a source of formaldehyde is used n is 0 in structure (I) and X and Y are nitrile, carboxylic acid, carboxylic acid esters, or X is nitro and Y is carboxylic acid ester, or X is nitrile and Y is carboxylic acid ester, the latter combination giving rise to 2-cyanoacrylates using alkyl cyanoacetates as a substrate, for example. When acrolein is used, n is 1 and the same combinations of X and Y can apply in structure (I).

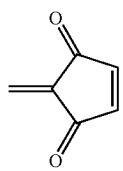

II

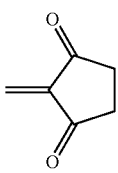

III

When a source of formaldehyde is used, structures (II) and (III) would result when cyclopentene diones, cyclohexene diones, cyclopentane diones or cyclohexane diones are used. When acrolein is used, the methylene bond would be conjugated to another alkene group (by analogy to structure (I) above).

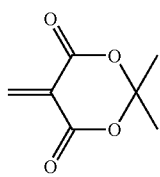

IV

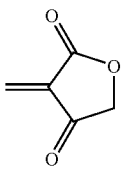

V

When a source of formaldehyde is used, structures (IV) and (V) would result when Meldrum's acid and tetronic acid are used. When acrolein is used the methylene bond again would be conjugated to another alkene group (by analogy to structure (I) above).

The initial reactant and the second reactant are placed in a polar solvent in order to conduct the synthesis. The polar solvent ordinarily comprises an ionic liquid; that is a salt whose melting point is less than 100° C., which in its molten form contains only ions. These polar solvents may optional include a minor amount of water, though in most cases they will be substantially anhydrous.

Examples of certain ionic liquids that may be useful in the present invention include the cation allyl ("AMIM") and/or butyl methylimidiazole ("BMIM"). As an anion associated with the cation, $X^-$ may be $PF^-_6$, $BF^-_4$, $SbF_6^-$ or other anions described as 'soft' due to declocalisation of charge over several atoms. Other examples of ionic liquids include ethylenediammonium diacetate, ethylammonium nitrate, n-butyl pyridinium nitrate.

In addition to the counterions noted above, phosphate counterions, anions derived from triethylborohydride and thioglycolic acid are also contemplated, such as alkyl or $BMIM^+BEt_3^-$.

The electron deficient olefin so formed by the inventive processes may be a variety of olefins having at least one electron withdrawing group attached thereto. In a desirably embodiment, as noted above with respect to the second reactant, the electron deficient olefin so formed will have two or more electron withdrawing groups attached thereto, which may be the same or different. Particularly desirable products have two electron withdrawing groups attached thereto which are different, such as 2-cyanoacrylate esters.

Representative examples of 2-cyanoacrylate esters so formed by the inventive processes include methyl, ethyl, n-propyl, i-propyl, propargyl, n-butyl, i-butyl, n-pentyl, n-hexyl, 2-ethylhexyl, n-octyl, n-nonyl, oxononyl, n-decyl, n-dodecyl, allyl, ethynyl, 2-butenyl, cyclohexyl, phenyl, phenethyl, tetrahydrofurfuryl, chloroethyl, 2,2,2-trifluoroethyl, hexafluoroisopropyl, methoxymethyl, methoxyethyl, methoxybutyl, ethoxyethyl, propoxyethyl, butoxymethyl, butoxyethyl and dimethyl siloxane esters of 2-cyanoacrylic acid.

The reaction of the present invention may proceed under mild heating conditions, without heat at room temperature or even at sub room temperature and sub zero temperatures, depending of course on the specific reactants and the scale of the reaction. The reaction requires some temperature to decompose the source of formaldehyde, e.g., paraformaldehyde may be gently heated up to 70° C., to liberate formaldehyde in situ in the reaction medium. The temperature may be reached through an external heating element or internally by means of the exotherm that may be generated depending on the identity of the reactants. The temperature of the reaction is controlled to accommodate such exothermic processes and cooling may be applied even to sub-ambient or sub-zero temperatures where the ionic liquid solvent remains liquid, but by-products like water for example solidify and may be separated.

The time of reaction may be monitored by reference to the formation of the desired product. Infrared spectrometer is a particularly useful tool in this regard. The time may be as little as 30 minutes, for instance, or longer or shorter for that matter depending again on the specific reactants, the scale of the reaction and whether heat is added to the reaction conditions.

Once formed, the product of the reaction may be isolated by direct distillation under vacuum out of the reaction mixture or by freezing it in a solid form and separating off the liquid phase. This is particularly so in the case of 2-cyanoacrylates (particularly their lower esters) which are relatively volatile whereas ionic liquid solvents are noted for their lack of volatility.

The electron deficient olefin so formed by the inventive processes may be stabilized during the synthesis and or isolation procedure and also in the isolated product to improve its shelf life. Suitable stabilizes include anionic stabilizers and free radical stabilizers.

For example, free radical stabilizers include hydroquinone, pyrocatechol, resorcinol or derivatives thereof, such as hydroquinone monoethyl ether, or phenols, such as di-t-butylphenol or 2,6-di-t-butyl-p-cresol, 2,2'-methylene-bis-(4-methyl-6-t-butylphenol), bisphenol A, dihydroxydiphenylmethane, and styrenized phenols.

For example, anionic stabilizers include Lewis acids, sulfuric acid, hydrochloric acid, sulfonic acids, such as methane, ethane or higher sulfonic acids, p-toluene sulfonic acid, phosphoric acid or polyphosphoric acids, silyl esters of strong acids, such as trialkyl chlorosilanes, dialkyl dichlorosilanes, alkyl trichlorosilanes, tetrachlorosilane, trialkyl silylsulfonic acids, trialkyl silyl-p-toluene sulfonates, bis-trialkyl silylsulfate and trialkyl silylphosphoric acid esters.

The amount of either stabilizer used to stabilize the electron deficient olefin prepared by the inventive processes is well known to those of ordinary skill in the art, and may be varied depending on the properties of the resulting composition made from the so formed electron deficient olefin.

The following example is used to illustrate but in no way limit the present invention.

EXAMPLE

Example 1

A 500 ml, three necked flask is fitted with a stirrer a pressure equalising dropping funnel, a Dean Stark water trap and a reflux condenser.

Previously and carefully dried ionic liquid, 1-butyl-3-methylimidiazolium hexafluorophosphate ([BMIM]PF$_6$), approximately 70 mls and containing some paraformaldehyde (23 g), are added to the flask with stirring. Gentle heating may be introduced to assist in uniformly suspending the paraformaldehyde to give a slightly viscous opaque white suspension. n-Butylcyanoacetate (100 g) is added to the dropping funnel. The cyanoacetate is added to the flask at a constant rate over a 20 minute time interval while heating if necessary for a period of up to 30 minutes. Methane sulphonic acid and/or SO$_2$ as an anionic stabilizer could be added to the reaction mixture to prevent premature polymerisation, or the N-butylcyanoacrylate monomer could be distilled out of the reaction mixture directly once formed onto the anionic stabilizer.

What is claimed is:

1. A process for the preparation of a reactive electron deficient olefin, steps of which comprise
   (a) providing as reactants an aldehyde compound having the structure R—CH=O, wherein R is hydrogen or vinyl, or a source of said aldehyde compound and a compound containing a methylene linkage having at least one electron withdrawing substituent attached thereto, wherein the electron withdrawing substituent is selected from the group consisting of nitrile, carboxylic acids, carboxylic esters, sulphonic acids, ketones and nitro, in a solvent comprising an ionic liquid;
   (b) reacting the mixture of reactants under appropriate conditions and for a time sufficient to yield a reactive electron deficient olefin; and
   (c) separating from the mixture the so formed reactive electron deficient olefin to yield the reactive electron deficient olefin.

2. A process for the preparation of a reactive electron deficient olefin, steps of which comprise (a) providing as reactants an aldehyde compound having the structure R—CH═O, wherein R is hydrogen or vinyl, or a source of said aldehyde compound and a compound containing a methylene linkage having at least one electron withdrawing substituent attached thereto, wherein the electron withdrawing substituent is selected from the group consisting of nitrile, carboxylic acids, carboxylic esters, sulphonic acids, ketones and nitro, in a solvent comprising a salt whose melting point is less than 100° C., which in its molten form contains only ions;

(b) reacting the mixture of reactants under appropriate conditions and for a time sufficient to yield a reactive electron deficient olefin; and (c) separating from the mixture the so formed reactive electron deficient olefin to yield the reactive electron deficient olefin.

3. A process for the preparation of a 2-cyanoacrylate ester, steps of which comprise (a) providing as reactants an aldehyde compound having the structure H—CH═O, a 2-cyanoacetate, in a substantially anhydrous polar solvent comprising an ionic liquid;

(b) reacting the mixture of reactants under appropriate conditions and for a time sufficient to yield a 2-cyanoacrylate ester; and (c) separating from the mixture the so-formed 2-cyanoacrylate ester to yield 2-cyanoacrylate ester.

4. The process of claim 1, wherein the electron deficient olefin is a cyanoacrylate or a cyanopentadienoate.

5. The process of claim 1, wherein the compound containing a methylene linkage having at least one electron withdrawing substituent attached thereto is an ester of cyanoacetic acid.

6. The process of claim 1, wherein the aldehyde compound or a source of said aldehyde compound is paraformaldehyde, 1,3,5-trioxan, or acrolein.

7. The process of claim 1, wherein the electron deficient olefin is a biscyanoacrylate, biscyanopentadienoate or a bis-alkylene derived from dimalonates or malononitrile.

8. The process of claim 1, wherein the electron deficient olefin is a compound having one end terminating with a cyanoacrylate, cyanopentadienoate, or alkylene derived from dimalonate and another end terminating with a group selected from the group consisting of acrylates, siloxanes, blocked isocyanates, and epoxies.

9. The process of claim 1, wherein the 2-cyanoacrylates are selected from the group consisting of methyl, ethyl, n-propyl, i-propyl, propargyl, n-butyl, i-butyl, n-pentyl, n-hexyl, 2-ethylhexyl, n-octyl, n-nonyl, oxononyl, n-decyl, n-dodecyl, allyl, ethynyl, 2-butenyl, cyclohexyl, phenyl, phenethyl, tetrahydrofurfuryl, chloroethyl, 2,2,2-trifluoroethyl, hexafluoroisopropyl, methoxymethyl, methoxyethyl, methoxybutyl, ethoxyethyl, propoxyethyl, butoxymethyl, butoxyethyl and dimethylsiloxane esters of 2-cyanoacrylic acid.

10. The process of claim 3, wherein the 2-cyanoacrylates are selected from the group consisting of methyl, ethyl, n-propyl, i-propyl, propargyl, n-butyl, i-butyl, n-pentyl, n-hexyl, 2-ethylhexyl, n-octyl, n-nonyl, oxononyl, n-decyl, n-dodecyl, allyl, ethynyl, 2-butenyl, cyclohexyl, phenyl, phenethyl, tetrahydrofurfuryl, chloroethyl, 2,2,2-trifluoroethyl, hexafluoroisopropyl, methoxymethyl, methoxyethyl, methoxybutyl, ethoxyethyl, propoxyethyl, butoxymethyl, butoxyethyl and dimethylsiloxane esters of 2-cyanoacrylic acid.

11. The process of claim 2, wherein the electron deficient olefin is a cyanoacrylate or a cyanopentadienoate.

12. The process of claim 2, wherein the compound containing a methylene linkage having at least one electron withdrawing substituents attached thereto is an ester of cyanoacetic acid.

13. The process of claim 2, wherein the aldehyde compound or source of said aldehyde compound is paraformaldehyde, 1,3,5-trioxan, or acrolein.

14. The process of claim 2, wherein the electron deficient olefin is a biscyanoacrylate, biscyanopentadienoate or a bis-alkylene derived from dimalonates or malononitrile.

15. The process of claim 2, wherein the electron deficient olefin is a compound having one end terminating with a cyanoacrylate, cyanopentadienoate, or alkylene derived from dimalonate and another end terminating with a group selected from the group consisting of acrylates, siloxanes, blocked isocyanates, and epoxies.

16. The process of claim 2, wherein the 2-cyanoacrylates are selected from the group consisting of methyl, ethyl, n-propyl, i-propyl, propargyl, n-butyl, i-butyl, n-pentyl, n-hexyl, 2-ethylhexyl, n-octyl, n-nonyl, oxononyl, n-decyl, n-dodecyl, allyl, athynyl, 2-butenyl, cyclohexyl, phenyl, phenethyl, tetrahydrofurfuryl, chloroethyl, 2,2,2-trifluoroethyl, hexafluoroisopropyl, methoxymethyl, methoxyethyl, methoxybutyl, ethoxyethyl, propoxyethyl, butoxymethyl, butoxyethyl and dimethylsiloxane esters of 2-cyanoacrylic acid.

\* \* \* \* \*